United States Patent [19]

Biesel et al.

[11] Patent Number: 5,445,593
[45] Date of Patent: Aug. 29, 1995

[54] METHOD AND APPARATUS FOR THE CONTINUOUS CONDITIONING OF A CELL SUSPENSION

[75] Inventors: Wolfgang Biesel, Ottweiler; Bernd Mathieu; Wolfram Weber, both of Spiesen-Elversberg, all of Germany

[73] Assignee: Fresenius AG, Bad Homburg, Germany

[21] Appl. No.: 93,491

[22] Filed: Jul. 16, 1993

[30] Foreign Application Priority Data

Aug. 14, 1992 [DE] Germany ............. 42 26 974.1

[51] Int. Cl.⁶ ................................. B04B 7/08
[52] U.S. Cl. ............................. 494/43; 494/45
[58] Field of Search ............ 494/18, 45, 43, 35, 494/36, 37, 16, 17, 85; 604/408, 410

[56] References Cited

U.S. PATENT DOCUMENTS

| | | |
|---|---|---|
| 4,010,894 | 3/1977 | Kellogg et al. . |
| 4,014,329 | 3/1977 | Welch et al. . |
| 4,386,730 | 6/1983 | Mulzet ............... 494/45 |
| 4,447,221 | 5/1984 | Mulzet ............... 494/45 |
| 4,647,279 | 3/1987 | Mulzet ............... 494/45 |
| 4,886,487 | 12/1989 | Solem et al. . |
| 4,934,995 | 6/1990 | Cullis ................ 494/18 |
| 5,114,396 | 5/1992 | Unger ................. 494/45 |

FOREIGN PATENT DOCUMENTS

| | | |
|---|---|---|
| 0155684 | 10/1990 | European Pat. Off. . |
| 2262856A | 3/1979 | Germany . |
| 3817664C2 | 4/1990 | Germany . |
| WO8901792 | 3/1989 | WIPO . |

*Primary Examiner*—Robert W. Jenkins
*Attorney, Agent, or Firm*—Whitham, Curtis, Whitham & McGinn

[57] ABSTRACT

A method and apparatus for the continuous conditioning of a cell suspension, more particularly whole blood, in order to obtain an erythrocyte concentrate which is returned to the patient by autotransfusion. In accordance with the invention there are three treatment stages, that is to say sedimentation of the cell suspension, the addition of washing solution to the cell concentrate and renewed sedimentation and separation of the washing solution.

11 Claims, 3 Drawing Sheets

Course of Separation

Course of Separation

METHOD AND APPARATUS FOR THE CONTINUOUS CONDITIONING OF A CELL SUSPENSION

BACKGROUND OF THE INVENTION

The invention relates to a method for the continuous conditioning of a cell suspension, in the case of which the cell suspension is centrifuged and the separated components of the cell suspension are separately removed.

The invention furthermore relates to an apparatus for performing a method for the conditioning of a cell suspension, more particularly the above mentioned method, comprising a centrifuge, which has at least one separation chamber with an annular duct, a supply duct for the cell suspension, a drain duct for a high purity cell concentrate to be produced and a drain duct for components of the cell suspension which are not needed.

In the prior art many proposals have been made for such separation apparatus and corresponding method, in the case of which more particularly blood is separated into its components and the latter, for instance erythrocytes or plasma, are put to a further use.

There are many medical applications for such methods and apparatus. One of these fields of application is intraoperative autotransfusion, which represents a transfusion technique economizing in the use of extraneous blood and which has found wide application in the last ten years. Intraoperative autotransfusion is a method for the retransfusion of blood collected from the operation site. Within the field of intraoperative autotransfusion so-called "whole blood transfusion methods" are able to be employed which only involve particle filtration of the collected blood, while more involved methods are the plasma separation and washing methods, which lead to a washed erythrocyte concentrate for retransfusion. The advantages of transfusion of autologous blood, that is to say blood from the patient as opposed to blood from another source (homologous blood) lie in the prevention of infectious diseases such as for example AIDS, hepatitis or others, and furthermore in the prevention of transfusion reactions owing to biological incompatibility and immune system reactions.

As part of the development of intraoperative autotransfusion techniques it has been found that transfusion of whole blood may have disadvantages as compared with transfusion of washed erythrocyte concentrates. These disadvantage of whole blood transfusion methods are that undesired components of the collected blood cannot be eliminated. Intraoperative blood contains unknown quantities of hemolysis products, extraneous components leached into the tissues or coming from the outside, excess volume, anticoagulants, activated plasmatic and cellular coagulation factors, products resulting from coagulation activation and of the fibrinolytic system. All these components may be responsible for clinical complications which in turn lead to a limitation of the field of application. In the prior art there have been suggestions to utilize filter systems in such autotransfusion systems for blood, which however only retain blood clots or pieces of tissue. Such a system is proposed in the U.S. Pat. No. 4,014,329. The U.S. Pat. No. 4,886,487 describes an apparatus for the separation of excess fluid, in which respect however coagulation factors, washing liquid, anticoagulant and other additives are returned with the blood to the patient.

As an alternative to whole blood transfusion plasma separation methods and plasma separation methods in combination with washing methods, or washing methods alone, have been developed, which use centrifuges. Such method are described in the German patent publication 2,262,856 A and the patent publication WO 89/01792. These centrifuges do however suffer from the disadvantage that they operate discontinuously. The individual method steps for the treatment of the blood and for retransfusion take place one after each other in time, such treatment having to take place in relatively large units with a completely filled chamber in order to ensure the functional operability of the method. Thus for example it is necessary to collect 225 ml of erythrocyte concentrate in a centrifuge.

The disadvantages of such discontinuous methods of operating are to be seen more specifically in the large initial volume, which is necessary for each respective conditioning stage. The treatment of small quantities, as is for instance necessary in pediatrics, is consequently not possible at all. A further, substantial disadvantage of such discontinuously operating methods is to be seen in the slow rate of processing, which is caused by the sequential performance of the individual method steps.

It is therefore to be seen that known methods and equipment are not suitable for continuous conditioning of a cell suspension as necessary in the case of an intraoperative autotransfusion.

The German patent publication 3,817,664 C describes a counter-current extraction centrifuge in which whole blood is centrifuged in the opposite direction to a washing solution. Neither the apparatus nor the method are however able to fulfill the requirements which arise in the case of autotransfusion, since undesired components are not separated in a reliable and effective manner.

The most relevant prior art as regards the apparatus is constituted by the European patent publication 155 684 B1, which describes a device for the separation of blood and provides for a return of low-thrombocyte plasma in order to dilute the whole blood feed. For the fields of application in question this equipment is however not able to be employed, since there is no suitable supply duct system in the separation chamber here.

The U.S. Pat. No. 4,010,894 shows a centrifuge with an annular duct, which renders possible a multi-stage manner of operation with the possibility of separate removal of red blood cells, plasma and further blood components. This device is not suitable for the purpose of the invention either, because there is no sufficient separation of the desired components of the cell suspension. The cell concentrate can not be subjected to a washing operation, something that is essential for sufficient separation.

SHORT SUMMARY OF THE INVENTION

One object of the invention is to provide a method and an apparatus of the type initially mentioned, which while having a simple structure and being simple and reliable to use renders possible an effective separation of undesired components of the blood suspension.

A further object of the invention is to provide such a system which operates continuously.

Another object of the invention is to create a method and apparatus with which the conditioning of small volumes of cell suspension is possible, such conditioning taking place with a high efficiency and in a short time.

In accordance with the invention, as regards the method, the object of the invention is attained since cells of the cell suspension are continuously concentrated and the concentrated cells are resuspended in a washing solution and the remaining components are separated from the cells.

The method in accordance with the invention is characterized by a series of considerable advantages. In accordance with the invention there is in fact a continuous method for the separation of one sort of cells, in the case of which the desired type of cell, preferably erythrocytes, is separated from the cell suspension by centrifugation. After this the cell concentrate is washed by resuspension in the washing solution. Then the spent washing solution is separated by further centrifuging. It is therefore possible in a very effective manner to obtain the desired components of the cell suspension with a high concentration and with a high degree of purity. Therefore the method is more particularly suitable for the intraoperative conditioning of blood and reinfusion without danger. The method in accordance with the invention operates continuously and only requires small initial volumes: it is possible to operate with a high blood throughput rate and consequently a high conditioning rate for erythrocyte concentrate (60–100 ml/min) at low pumping rates which do not damage the blood. Furthermore it is possible to use the erythrocyte concentrate for direct reinfusion. A further, substantial advantage of the three-stage, continuously operating method resides in the reduction in the time necessary for the overall process by at least a factor of 2.

In accordance with the method of the invention there is a provision for the concentration of the cells to take place down to hematocrit readings of 50 to 70%. This means that there is a separation of at least 95% of the original quantity of plasma in the whole blood supplied.

As a washing solution it is possible to use an isotonic sodium chloride solution, Ringer's solution or the like.

The method in accordance with the invention may be normally typically performed in the following manner.

Blood, typically with a hematocrit reading of 10 to 30%, is aspirated from the operation site, anticoagulated, filtered and temporarily stored in a container. The blood is supplied via a supply duct into a separation chamber and separated in accordance with density thereof into its components and the separated plasma is drawn off. In a second method stage the concentrated cell fraction (more particularly erythrocyte concentrate) is resuspended by the continuous addition of a washing solution. In the following, repeated separation the remaining, non-cellular components are drawn off and owing to the removal of the spent washing solution the result is a very pure erythrocyte concentrate.

In accordance with the invention the object as regards the separation equipment is attained by the provision of a supply duct for a washing solution in addition to the already mentioned ducts.

In accordance with a further development of the apparatus of the invention there is the provision for the apparatus to have a first zone for the separation of the cell suspension, a second zone for resuspension and a third zone for renewed separation of the resuspended cells. The separation chamber may in accordance with the invention be designed in one single part, in two parts or even in three parts. It is possible to design the separation chamber as a self-supporting, rigid structure. Furthermore it can be designed as disposable, recyclable part.

The supply duct of the washing solution is in accordance with the invention so arranged in a convenient manner that the washing solution is caused to flow in counter-current. In this respect it may be appropriate for the drain duct for the spent washing solution to be made integral with the drain duct for components which are no longer required. This will mean that the apparatus is simpler in structure and in its technical features.

Further advantageous developments and convenient forms of the novel separation apparatus will be understood from the following detailed descriptive disclosure of embodiments thereof in conjunction with the accompanying drawings.

LIST OF THE SEVERAL VIEWS OF THE FIGURES

DETAILED ACCOUNT OF WORKING EMBODIMENTS OF THE INVENTION

Figure 1:
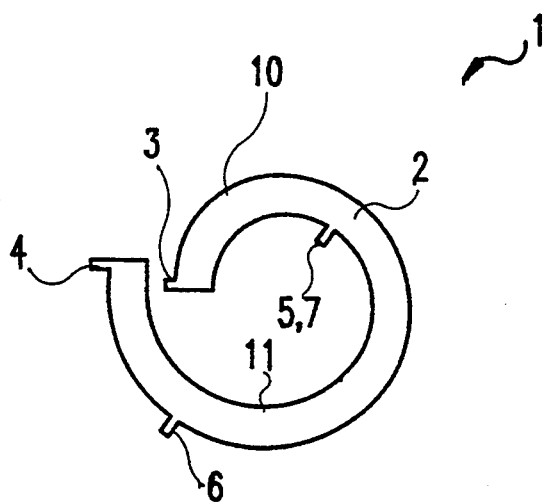
FIG. 1 is a diagrammatic plan view of one embodiment of the novel separation chamber.

In FIG. 1 the reader will see a diagrammatic view of a separation chamber 1, which surrounds a spiral annular duct 2. This annular duct may be designed to be radially symmetrical or in the form of a spiral. For instance, on one outer side 10 of the annular duct 2 in this case a supply or feed duct 3 for cell concentrate, for example whole blood, is arranged here. On the outer side 10 of the annular duct 2 a drain duct 4 for cell concentrate (erythrocyte concentrate) is arranged, the removal of the erythrocytes being performed centrifugally. In the middle zone or, respectively, in the terminal zone of the annular duct 2 a supply duct 6 is provided for washing solution, the washing solution being supplied anti-centrifugally. On an inner side 11 of the annular duct 2 there is a drain duct 5 for components (plasma) no longer required, which duct is made integrally with a drain duct 7 for spent or dirty washing solution. These outlets may be arranged in the center of the annular duct 2, but however they may be furthermore arranged in the part extending as far as the outlet for the cleaned erythrocyte concentrate and as far as the blood inlet.

Figure 2:
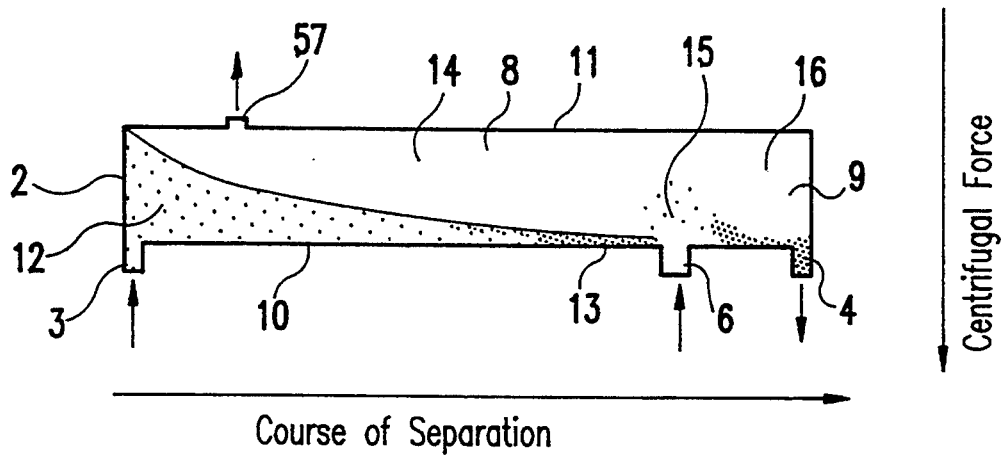
FIG. 2 is a diagrammatic, developed functional view of events in the separation chamber depicted in FIG. 1.

FIG. 2 shows the course of separation of the blood in the separation chamber depicted in FIG. 1, the events taking place in separation or the course of separation being plotted in the opposite direction to the direction of the centrifugal force. In the left hand part of FIG. 2 the supply of whole blood is represented by the supply duct 3, the whole blood 12 collects in the annular duct 2 is separated by the effect of centrifugal force in a first zone 8, the erythrocytes settling on the outer side 10 of the annular duct 2. On the other hand the plasma 14 is continuously led off through the drain duct 5.

In the zone, in which the erythrocyte concentrate has a hematocrit reading of more than 60% there is a supply of washing solution through the supply duct 6, also against the centrifugal force direction, such washing solution being mixed, owing to the radial direction of supply, in a mixing zone 15 with the erythrocyte concentrate in an optimum manner.

During the further course of separation the erythrocytes 13 are separated in a second zone 9 from the spent washing solution 16, which is removed via the drain duct 7. The drain ducts 5 and 7 are in this case made integrally. The cleaned erythrocyte concentrate is drained off through the drain duct 4 and supplied to the patient.

Figure 3:
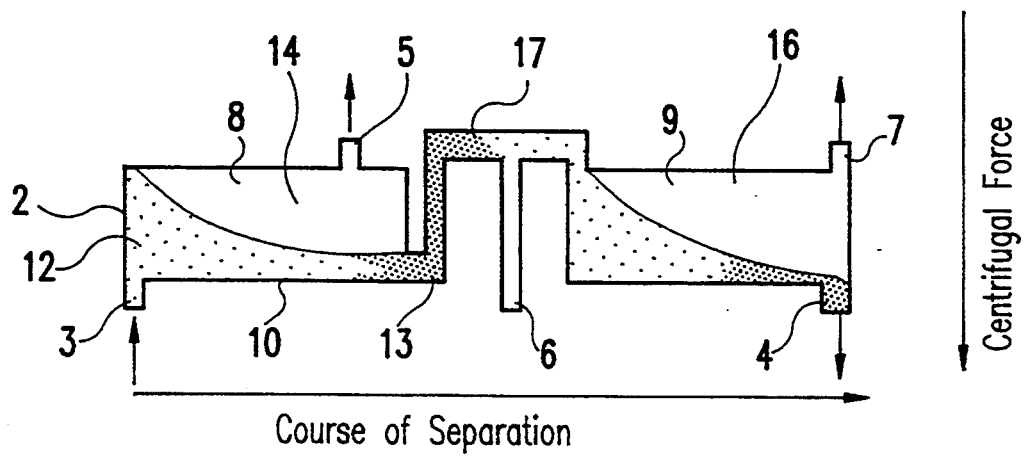
FIG. 3 is a developed, diagrammatic view of the functions in a further working embodiment of the separation chamber in accordance with the invention.

FIG. 3 shows a modification of the design, in the case of which the chamber is designed in two stages. As in the first working embodiment in accordance with FIG. 2 the whole blood (12) is supplied through the supply duct 3 from the outer side 10 of the annular chamber 2. The erythrocyte concentrate 13 is drawn off through a duct 17, whereas the plasma is let off via the drain duct 5. Adjacent to the duct 17 the supply duct 6 of the washing solution is provided, in which the latter is mixed the erythrocyte concentrate. After the following separation in the second part 9 of the zone the erythrocyte concentrate is removed through the drain duct 4, whereas the spent washing solution 16 is removed through the drain duct 7.

Figure 4:
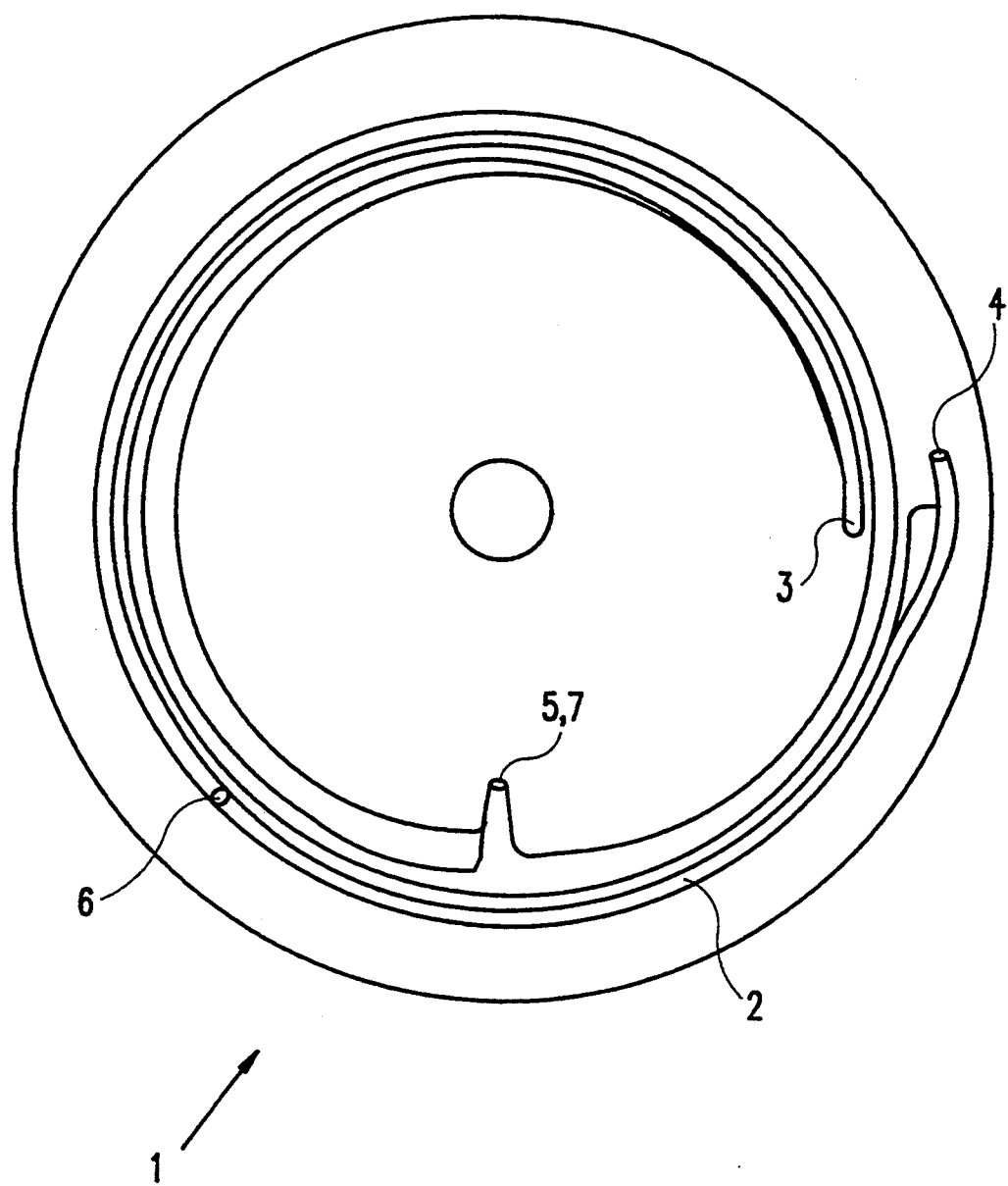
FIG. 4 is a plan view with details of construction of the separation in accordance with the invention.

FIG. 4 shows in a plan view details of the design of a spiral separating chamber 1, this working embodiment being substantially the same in structure as the working embodiment depicted in FIGS. 1 and 2.

Figure 5:
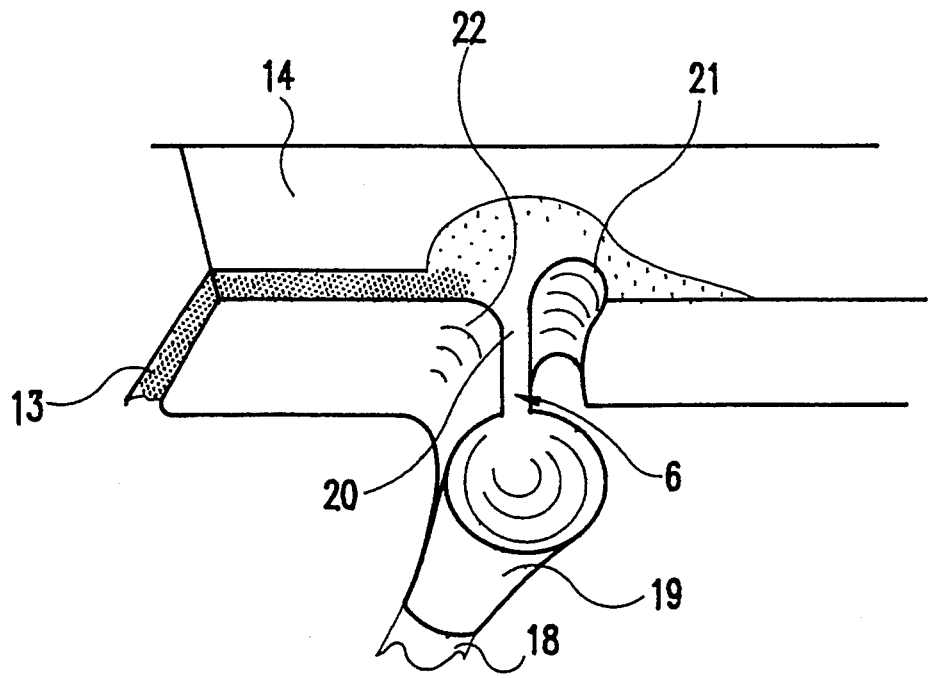
FIG. 5 is a partly perspective elevation on a larger scale of the design input port for the washing solution.
Figure 6:
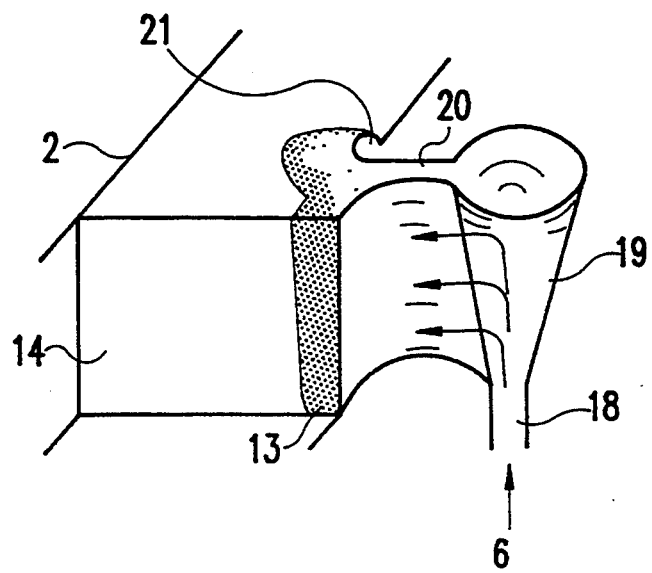
FIG. 6 is a side elevation of the design illustrated in FIG. 5.

FIGS. 5 and 6 show in perspective part of the design of the supply duct 6 for the washing solution. For the sake of clarity the erythrocytes 13 and the plasma 14 are illustrated, the attention of the reader being called to FIG. 2 as well. In the case of the working embodiment depicted in FIGS. 5 and 6 washing solution is supplied through a hose or pipe 18 to a conical body 19, the supply being to the lower zone, which has a reduced diameter, of the conical body 19. The latter is connected via a plate-like rib, which is naturally made hollow, with the interior space in the separation chamber. Considered in the direction of separation (see FIG. 2) the hollow rib 20 is adjoined by a bulge 21 directed into the interior of the annular duct 2, which bulge to a certain extent constitutes a dam. On the other hand the edge, which is opposite the dam 22, of the hollow rib is rounded off. This design renders possible an even entry flow of the washing solution along the full height of the gap. This leads to a turbulent flow and consequently to an even, thorough mixing. The hollow rib or gap 20 is for example 0.5 to 20 mm in width.

Although the above account has been limited to a few desired embodiments of the invention, this has not been with the intention of limiting the invention thereto. In fact a man in the art will have available a large number of possibilities in order to implement the common inventive principle and in order to adapt to particular circumstances of an individual case, more particularly in order to ensure an intimate contact between the cells and the washing solution, that is to say mixing s as complete as possible. As regards the quantity of the washing solution there are various possibilities of metering in a manner dependent on the individual case of application. In a normal case the quantity of washing solution is approximately equal to ten times the residual plasma. In the case of very impure or damaged blood however other dilution rates are advantageous.

We claim:

1. A centrifuge separation apparatus for treating a cell suspension in order to produce a highly purified cell concentrate comprising:
    at least one substantially annular separation chamber,
        said chamber being subdivided into first, second and third zones,
        said first zone for separation of the cell suspension and including an inlet located at a first end of said chamber for receiving the cell suspension,
        said second zone for resuspension of the cells and including an inlet for a washing solution,
        said third zone for separation of the resuspended cells and including an outlet for the cell concentrate located at a second end of said chamber,
    wherein the outlet for the cell concentrate is arranged on a same radial surface of said chamber as the inlet for the washing solution, and
    wherein at least one further outlet is arranged on a radial surface of said chamber opposite that of said same radial surface.

2. The separation apparatus as claimed in claim 1, wherein the at least one further outlet includes an outlet for evacuation of spent washing solution and for evacuation of a predetermined component of said cell suspension.

3. The separation apparatus as claimed in claim 1, wherein an outlet of said at least one further outlet being for evacuation of spent washing solution,
    wherein the inlet for the washing solution is arranged one of upstream from and downstream from the outlet of said at least one further outlet for spent washing solution thereby producing counter-current flow of the washing solution through the apparatus.

4. The separation apparatus as claimed in claim 1, wherein an outlet of said at least one further outlet being for evacuation of spent washing solution,
    wherein the outlet of said at least one further outlet for the spent washing solution is integrally formed with an outlet of said at least one further outlet for predetermined components of said cell concentrate.

5. The separation apparatus as claimed in claim 1, wherein the separation chamber is formed to have one of a radially symmetrical, spiral and doubly spiral structure.

6. The separation apparatus as claimed in claim 1, wherein the inlet for the washing solution is positioned in said chamber for producing a flow opposite to a force of gravity and in a radial direction from outside to inside.

7. The separation apparatus as claimed in claim 1, wherein the separation chamber is formed to have an integral, unitary structure.

8. The separation apparatus as claimed in claim 1, wherein the separation chamber is formed to have a two-piece structure.

9. The separation apparatus as claimed in claim 1, wherein the separation chamber comprises a self-supporting and rigid material.

10. The separation apparatus as claimed in claim 1, wherein the separation chamber comprises a disposable recyclable material.

11. A centrifuge separation apparatus for treating a cell suspension in order to produce a highly purified cell concentrate comprising:

at least one substantially annular separation chamber, said chamber being subdivided into first, second and third zones, said first zone for separation of the cell suspension and including an inlet located at a first end of said chamber for receiving the cell suspension, said second zone for resuspension of the cells and including an inlet for a washing solution, said third zone for separation of the resuspended cells and including an outlet for the cell concentrate located at a second end of said chamber, the outlet for the cell concentrate being arranged on a same radial surface of said chamber as the inlet for the washing solution, wherein at least one further outlet is arranged on a radial surface of said chamber opposite that of said same radial surface, said at least one further outlet including an outlet for evacuation of spent washing solution and evacuation of a predetermined component of said cell suspension, the inlet for the washing solution being positioned in said chamber so as to provide means for producing a flow opposite to a force of gravity and in a radial direction from outside to inside.

* * * * *